US00PP37089P2

(12) United States Plant Patent
Grazzini

(10) Patent No.: US PP37,089 P2
(45) Date of Patent: Nov. 4, 2025

(54) ***HEMEROCALLIS* PLANT NAMED 'G221407'**

(50) Latin Name: *Hemerocallis hybrida*
Varietal Denomination: G221407

(71) Applicant: Garden Genetics llc, Columbus, OH (US)

(72) Inventor: Richard A. Grazzini, Columbus, OH (US)

(73) Assignee: Garden Genetics, Columbus, OH (US)

( * ) Notice: Subject to any disclaimer, the term of this patent is extended or adjusted under 35 U.S.C. 154(b) by 0 days.

(21) Appl. No.: 19/025,391

(22) Filed: Jan. 16, 2025

(51) Int. Cl.
*A01H 5/02* (2018.01)
*A01H 6/00* (2018.01)

(52) U.S. Cl.
USPC ..... Plt./312

(58) Field of Classification Search
USPC ..... Plt./312
CPC ..... A01H 5/02; A01H 5/00; A01H 6/00
See application file for complete search history.

(56) References Cited

PUBLICATIONS

IP Australia *Hemerocallis* 'Stella Tangerine' Application No. 2020/273 retrieved online at https://ipsearch.ipaustralia.gov.au/pbr/2020/273, 5 pp. (Year: 2025).*
Rodriguez-Enriquez et al. A new day dawning: *Hemerocallis* (daylily) as a future model organism, Annals of Botany Company retrieved online at http://aobplants.oxfordjournals.org/, 2012, 1-15, 16 pp. total. (Year: 2012).*

* cited by examiner

*Primary Examiner* — June Hwu

(57) ABSTRACT

A new and distinct cultivar of *Hemerocallis* plant named 'G221407' is disclosed, characterized by flowers of an apricot-orange color, with a yellow throat, a darker orange-red eye and a slight ruffle to the petal edge. 'G221407' is a diploid, dormant type daylily, losing foliage with frost each fall, and re-emerging from the crown in the following spring. 'G221407' grows quickly and vigorously following emergence from dormancy, showing a growth rate during bare-root production which exceeds most comparable daylilies. 'G221407' blooms continuously from first-flower in early June until hard frost in the autumn. Plants are observed winter-hardy through at least USDA Zone 5. The new variety is a *Hemerocallis,* normally used for outdoor ornamental purposes.

2 Drawing Sheets

Figure 1:
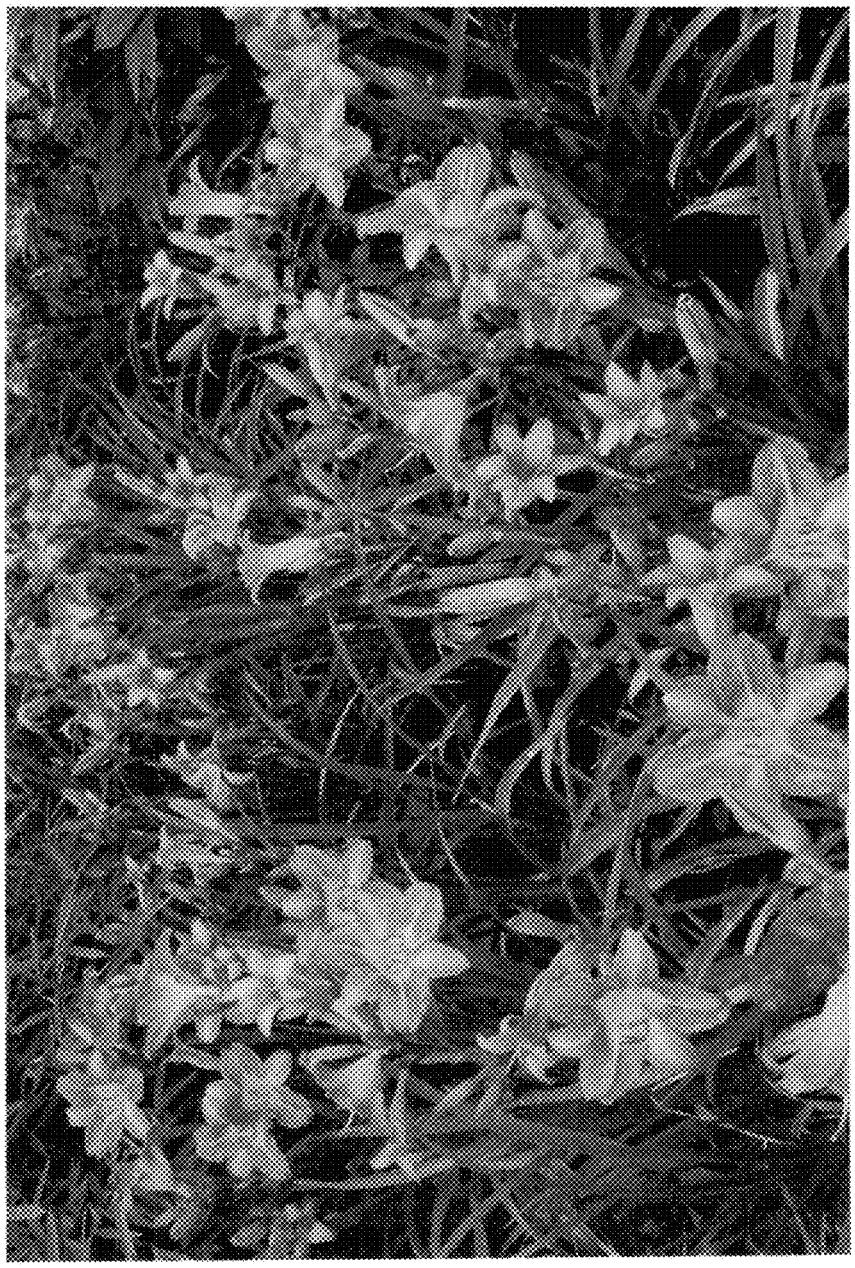

Latin name of the genus and species: *Hemerocallis hybrida.*
Variety denomination: 'G221407'.

BACKGROUND OF THE INVENTION

The new *Hemerocallis* cultivar is a product of a planned breeding program conducted by the inventor at a research nursery in Bellefonte, Pennsylvania. The self-pollination resulting in this new variety was made during 2011.

The parent is an unnamed, unpatented proprietary *Hemerocallis* variety. The new cultivar was selected in August of 2014 by the inventor in a group of seedlings resulting from the self-pollination, in a nursery in Bellefonte, Pennsylvania.

Asexual reproduction of the new cultivar was performed by division, at the same nursery in Bellefonte, Pennsylvania during August of 2014, and has shown that the unique features of this cultivar are stable and reproduced true to type in multiple successive generations.

SUMMARY OF THE INVENTION

The cultivar 'G221407' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G221407'. These characteristics in combination distinguish 'G221407' as a new and distinct *Hemerocallis* cultivar:

1. 'G221407' is a diploid, dormant type daylily, losing foliage with frost each fall, and re- emerging from the crown in the following spring.
2. 'G221407' has flowers of an apricot-orange color, with a yellow throat, a darker orange-red eye (distal to the throat), and a slight ruffle to the petal edge.
3. 'G221407' grows quickly and vigorously following emergence from dormancy, showing a growth rate during bare-root production which exceeds most comparable daylilies. The new cultivar produces 1.5 to 2 times the quantity of root divisions as 'Stella D'Oro' when grown under identical conditions.
4. 'G221407' fills retail and wholesale sales containers quickly, and then rapidly fills visual spaces in landscapes and gardens when planted in-ground.
5. 'G221407' blooms continuously from first flower in early June until hard frost in the autumn.
6. 'G221407' has been shown to be winter-hardy thru at least USDA zone 5.

PARENT COMPARISON

Plants of the new cultivar 'G221407' are similar to plants of the parent in most horticultural characteristics; however, plants of the new cultivar 'G221407' differ in the following:

1. 'G221407' blooms continuously from emergence thru hard autumnal frost. The parent variety repeat-blooms rather than remaining in constant bloom.
2. 'G221407' has a distinct dark orange-red eye above the flower throat. The parent variety does not display such a distinct eye.
3. 'G221407' has slight ruffled edges to its flower petals. The seed parent does not have ruffled petals.
4. 'G221407' grows and blooms throughout the season, assuming good growing conditions. Under similar conditions, the parent stopped producing new foliage by mid-summer.
5. 'G221407' is only mildly fragrant. The parent is strongly fragrant.

COMMERCIAL COMPARISONS

Plants of the new cultivar 'G221407' are comparable to the well-known commercial variety *Hemerocallis* 'Stella D'Oro', unpatented. The two *Hemerocallis* varieties are similar in most horticultural characteristics, however, the new variety 'G221407' differs in the following:

1. 'G221407' has apricot-orange-colored flowers, whereas 'Stella D'Oro' has yellow-gold-colored flowers.
2. 'G221407' has a distinct orange-red eye in its flower. 'Stella D'Oro' has no dark eye.
3. 'G221407' has a slight fragrance to its flowers. 'Stella D'Oro' has no fragrance.
4. 'G221407' produces bare-root divisions at a much higher rate than does 'Stella D'Oro'.
5. 'G221407' has a more ruffled edge to its flower petals than does 'Stella D'Oro'.

Plants of the new cultivar 'G221407' are comparable to the commercial variety *Hemerocallis* 'Happy Returns', unpatented. The two *Hemerocallis* varieties are similar in most horticultural characteristics, however, the new variety 'G221407' differs in the following:

1. 'G221407' has apricot-orange-colored flowers, whereas 'Happy Returns' has light yellow colored flowers.
2. 'G221407' has a distinct orange-red eye in its flower. 'Happy Returns' has no dark eye.
3. 'G221407' comes into first flower after emergence from dormance 3 to 5 days later than 'Happy Returns'.
4. 'G221407' produces bare-root divisions at a higher rate than does 'Happy Returns'.
5. 'G221407' has a more ruffled edge to its flower petals than does 'Happy Returns'.

Plants of the new cultivar 'G221407' are comparable to the commercial variety *Hemerocallis* 'Stella Tangerine', unpatented. The two *Hemerocallis* varieties are similar in most horticultural characteristics, however, the new variety 'G221407' differs in the following:

1. 'G221407' has apricot-orange-colored flowers with yellow streaks, whereas 'Stella Tangerine' has solid orange-colored flowers.

BRIEF DESCRIPTION OF THE PHOTOGRAPHS

The accompanying photograph in FIG. 1 illustrates a mass planting of typical flowering plant of 'G221407' grown outdoors in Bellefonte, PA at approximately 1 year old.

Figure 2:
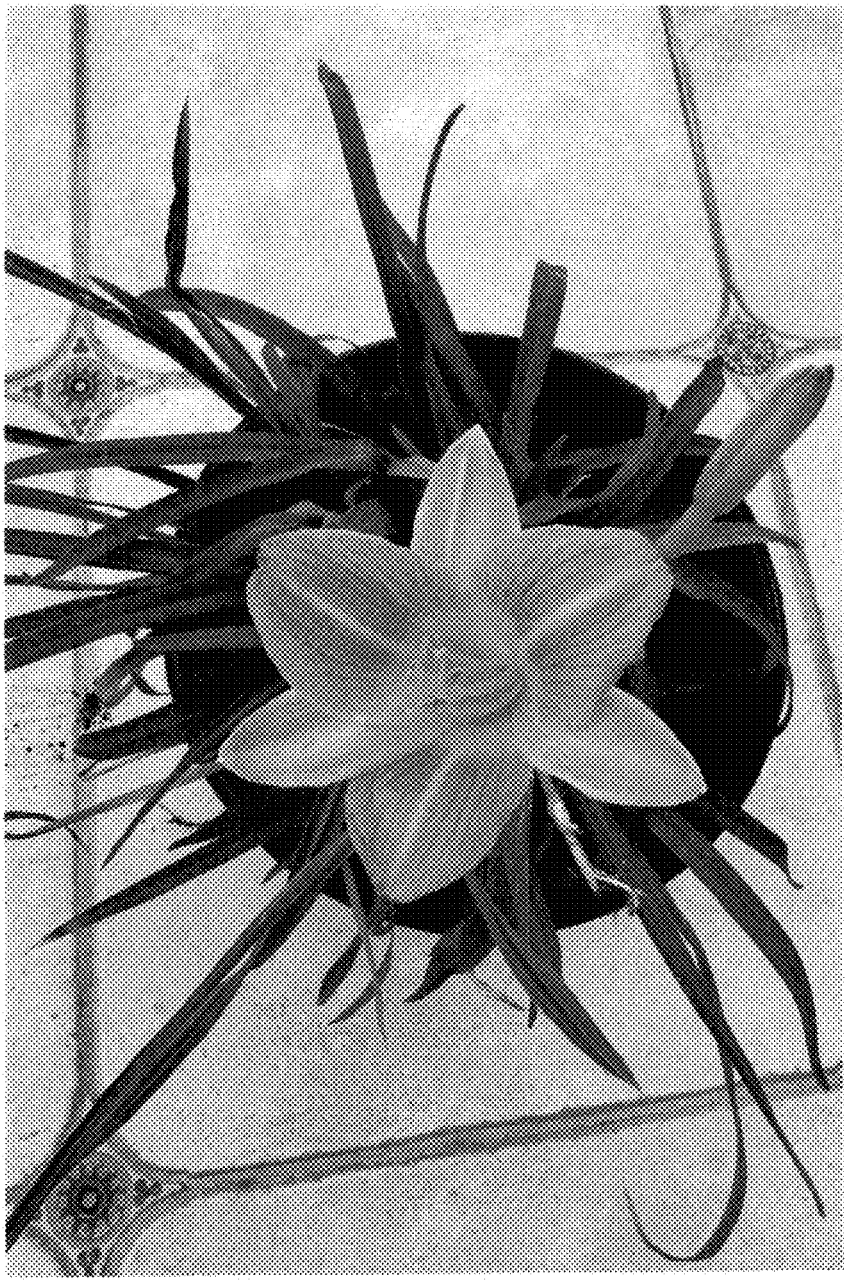

FIG. 2 illustrates a single flowering plant of 'G221407' grown outdoors in Camarillo, CA at around 8-months old in a 2-gallon pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'G221407' plants grown outdoors in Camarillo, California. The growing temperature ranged from approximately 10° C. to 25° C. during the day and from approximately 6° C. to 12° C. during the night. General light conditions are normal sunlight and numerical values represent averages of typical plant types. Measurements were taken during June of 2024.

Botanical classification: *Hemerocallis hybrida* 'G221407'.

ROOTS

Root description: Rhizomes. Thick, typically colored near Orange-White 159C.

PROPAGATION

Propagation method: Rhizome divisions or tissue culture.

PLANT

Age of plant described: Approximately 10 months.

Container size: 1 gallon.

Growth habit: Dormant hardy, perennial. In USDA Zones 5 and colder, all above ground foliage is lost in late Fall.

Height: Approximately 30 cm to top of highest leaf. Approximately 40 cm to top of highest inflorescence.

Plant spread: Approximately 45 cm.

Branching characteristics: Non-branching, forms basal clumps of foliage.

FOLIAGE

Leaf:

*Arrangement.*—Basal fan shaped clumps.

*Average length.*—Approximately 30 cm.

*Average width.*—Approximately 1.6 cm.

*Shape of blade.*—Narrow lanceolate.

*Apex.*—Acute.

*Base.*—Truncate.

*Sheathing.*—No.

*Margin.*—Entire.

*Texture of top surface.*—Glabrous with minute ridges.

*Texture of bottom surface.*—Glabrous with minute ridges and a very prominent mid-vein.

*Quantity of leaves per plant.*—Average 50.

*Color.*—Young foliage upper side: Near RHS Green 137A. Young foliage under side: Near RHS Green 137A. Mature foliage upper side: Near RHS Green 137A, base Yellow-green 144C. Mature foliage under side: Near RHS Green 137A, base Yellow-green 144C.

*Venation*.—Type: Parallel. Venation color upper side: Near RHS Green 137A. Venation color under side: Near RHS Green 137A.

FLOWER

Natural flowering season: Typically early June until first frost.

Inflorescence type and habit: Single flowers occurring in clusters of 2 to 4 on a scape.

Flower longevity on plant: 2 to 4 days from fully opened.

Quantity of open flowers per plant at one time: Approximately 5 to 12.

Inflorescence size (excluding scape):
- *Height*.—Approximately 8 cm.
- *Width*.—Approximately 11 cm.

Flower fragrance: Moderate floral scent.

Individual corolla:
- *Arrangement*.—Rotate, composed of 3 sepals and 3 petals, strongly overlapping.
- *Size*.—Length: Approximately 8.5 cm. Width: Approximately 7 cm at widest point.
- *Petals per corolla*.—3.
- *Sepals per corolla*.—3.
- *Petal length*.—4.5 cm.
- *Petal width*.—2.5 cm.
- *Sepal length*.—4.5 cm.
- *Sepal width*.—1.8 cm.
- *Sepal and petal margin*.—Entire, with slight ruffling.
- *Petal shape*.—Ovate.
- *Sepal shape*.—Lanceolate.
- *Petal apex*.—Broad acute, slightly ruffled.
- *Sepal apex*.—Acute, slightly ruffled.
- *Petal and sepal base*.—Truncate.
- *Petal and sepal texture*.—Glabrous, all surfaces.

Color:
- *Petals*.—When opening: Outer surface: Lower half Yellow-Orange 17D flushed 17C. upper half Orange-Red N34A. Vertical center line Yellow-14 Orange 17C. Inner surface: Large central eye (covering about half surface) Yellow-Orange 21B flushed Yellow 13A. From center to apex Orange-N34B with veins N34A. Fully opened: Outer surface: Near Lower two thirds Yellow-Orange 23B with veins N34B. Uppermost 1/3 N34C with Veins N34B. Inner surface: Large central eye (covering about half surface) Yellow-Orange 21B. From center to apex Orange-N34C with veins N34A. Vertical center line Yellow-Orange 17D.

Color:
- *Sepals*.—When opening: Outer surface: Lower half Yellow-Orange 17D flushed 17C. upper half Orange-Red N34A. Inner surface: Large central eye (covering about half surface) Yellow-Orange 21B flushed Yellow 13A. From center to apex Orange-N34B with veins N34A. Fully opened: Outer surface: Near Lower two thirds Yellow-Orange 23B with veins N34B. Uppermost 1/3 N34C with Veins N34B. Duffused Yellow-Orange 14C in the center of the uppermost 1/2. Inner surface: Large central eye (covering about half surface) Yellow-Orange 21B. From center to apex Orange-N34C with veins N34A. Lightly suffused Yellow-Orange 14C in the center of the uppermost 1/3.

Corolla tube:
- *Length*.—2.8.
- *Diameter*.—1.5 cm.
- *Color interior*.—Yellow-Orange 21B.
- *Color exterior*.—Yellow-Orange 14C.

Bud:
- *Shape*.—Elongated and oblong.
- *Length*.—Approximately 4 cm.
- *Diameter*.—Approximately 1.8 cm.
- *Color*.—Lower half Yellow-Orange 17D flushed 17C. upper half Orange-Red N34A.

Scape:
- *Length*.—24 cm to 28 cm.
- *Width*.—Approximately 5 mm.
- *Angle*.—Upright, straight.
- *Strength*.—Very Strong.
- *Color*.—Near RHS Green 137A.

Stem bracts:
- *Length*.—2.4 cm to 3.3 cm.
- *Width*.—Approximately 1 cm.
- *Shape*.—Irregular deltoid.
- *Color*.—Near RHS Green 137C.

Peduncles:
- *Quantity per scape*.—Typically 2 to 4.
- *Length*.—4_cm.
- *Width*.—4 mm.
- *Aspect/angle*.—Average range 25 to 45 degrees.
- *Texture*.—Glabrous.
- *Color*.—Near Green RHS 137A.

REPRODUCTIVE ORGANS

Stamens:
- *Number*.—Average 6.
- *Filament length*.—Approximately 4 cm.
- *Filament color*.—Near RHS Yellow-Orange 21A.
- *Protrusion*.—Anthers protrude approximately 1 cm beyond tepals.
- *Anther length*.—6 mm.
- *Anther color*.—Near RHS Yellow-Orange 23A.
- *Anther shape*.—Symmetrical and oblong.
- *Pollen*.—Abundant. Colored near Yellow-Orange 23A.

Pistil:
- *Number*.—1.
- *Length*.—Approximately 5.5 cm.
- *Style color*.—Near RHS Orange 25C.
- *Stigma*.—Shape: Linear. Color: Near RHS Yellow-Orange 23C.
- *Ovary color*.—Near Green RHS 137A.

OTHER CHARACTERISTICS

Seeds and fruits: None observed to date.

Disease/pest resistance: Neither resistance nor susceptibility to normal diseases and pests of *Hemerocallis* observed.

Temperature range: USDA Zones 5-10.

What is claimed is:

1. A new and distinct cultivar of *Hemerocallis* plant named 'G221407' as herein illustrated and described.

* * * * *